(12) United States Patent
Clark

(10) Patent No.: US 6,843,967 B2
(45) Date of Patent: Jan. 18, 2005

(54) CURING UNIT

(75) Inventor: Daniel P. Clark, Stamford, CT (US)

(73) Assignee: Pentron Laboratory Technologies, LLC, Wallingford, CT (US)

( * ) Notice: Subject to any disclaimer, the term of this patent is extended or adjusted under 35 U.S.C. 154(b) by 89 days.

(21) Appl. No.: 10/411,426

(22) Filed: Apr. 10, 2003

(65) Prior Publication Data

US 2003/0228243 A1 Dec. 11, 2003

Related U.S. Application Data

(60) Provisional application No. 60/371,881, filed on Apr. 11, 2002.

(51) Int. Cl.[7] .............................. B01J 19/08; A61C 3/00
(52) U.S. Cl. ................. 422/186; 422/186.3; 425/174.4; 433/29
(58) Field of Search ........................ 433/29; 425/174.4; 422/186, 186.3

(56) References Cited

U.S. PATENT DOCUMENTS

| | | | | |
|---|---|---|---|---|
| 6,077,073 A | * | 6/2000 | Jacob | 433/29 |
| 6,386,865 B1 | * | 5/2002 | Suh et al. | 433/27 |
| 2001/0046652 A1 | | 11/2001 | Ostler | 433/29 |
| 2002/0172918 A1 | | 11/2002 | Burtscher | 433/29 |
| 2002/0177098 A1 | | 11/2002 | Plank | 433/29 |

* cited by examiner

*Primary Examiner*—Steven VerSteeg
(74) *Attorney, Agent, or Firm*—Ann M. Knab

(57) ABSTRACT

A curing apparatus providing rapid curing by using light, pressure, pressure and light, or purge, pressure and light to cure resinous materials by application of energy from an external source to excite polymerization in a polymerizable system. A curing chamber is provided to house the polymerizable dental material. The apparatus utilizes light emitting diodes (LEDs) to radiate energy to polymerize the dental materials. The LEDs are positioned optimally within the curing apparatus to provide efficient, effective polymerization of the dental materials.

24 Claims, 7 Drawing Sheets

US 6,843,967 B2

CURING UNIT

CROSS-REFERENCE TO RELATED APPLICATIONS

This application claims priority to Provisional Application No. 60/371,881 filed Apr. 11, 2002 which is hereby incorporated by reference.

FIELD OF THE INVENTION

The present invention relates generally to light for a curing unit and more specifically to light for use in a curing unit for dental materials.

BACKGROUND OF THE INVENTION

Curing, as used herein, is the processing of a plastic or resinous material from a fluid or soft and compliant state to a permanent hard, durable and solid state. Conventionally, this is accomplished both by the elimination of solvents and by chemical changes involving interlinking of molecules commonly known as polymerization of the material. Of the two, polymerization is the more advantageous since it does not commonly involve dimensional changes and usually produces a substantial increase in the strength of the material. Polymerization is usually caused by the addition of activating chemicals (activators), by irradiation with some form of wave energy, either electric or electromagnetic in nature, or by applying heat, or by a combination thereof.

The use of incandescent lamps such as halogen lamps as light sources for a laboratory curing apparatus generate excessive unwanted heat and also have a short life span, typically 50 hours. The heat may melt the pressure vessel or heat the composite material above recommended temperatures. The incandescent lights are very power inefficient since most of the light is not needed and is the wrong wavelength for the photo-initiators used in the dental composite material. Components to remove the unwanted heat are usually necessary adding to the cost of the device.

It would be beneficial to provide a light source that is power efficient and does not overheat the composite material or vessel housing the composite. It would be advantageous to provide a light source that does not require additional components to eliminate unwanted heat such as fans, ducts, vents, thermal sensors and the like.

SUMMARY OF THE INVENTION

The above-described and other problems and deficiencies of the prior art are overcome or alleviated by the curing apparatus of the present invention, wherein rapid curing is provided by using light, pressure, pressure and light, or purge, pressure and light to cure resinous materials by application of energy from an external source to excite polymerization in a polymerizable system. A curing chamber is provided to house the polymerizable dental material. The apparatus utilizes light emitting diodes (LEDs) to radiate energy to polymerize the dental materials. The LEDs are positioned optimally within the curing apparatus to provide efficient, effective polymerization of the dental materials.

BRIEF DESCRIPTION OF THE DRAWINGS

Features of the present invention are disclosed in the accompanying drawings, whrerein similar reference characters denote similar elements throughout the several views, and wherein.

DESCRIPTION OF THE INVENTION

As will be appreciated, the present invention provides a new and improved curing apparatus for curing a polymerizable resinous material, such as a dental material. U.S. Pat. Nos. 4,873,446, 4,839,521, 5,040,964, and 4,309,617 are directed to polymerization and/or curing of materials and are hereby incorporated by reference. The dental material may include, but is not limited to at least one filled or unfilled resin having at least one ethylenically unsaturated group. Examples of the ethylenically unsaturated groups include acrylates, methacrylates, vinyl groups and combinations thereof.

Figure 1:
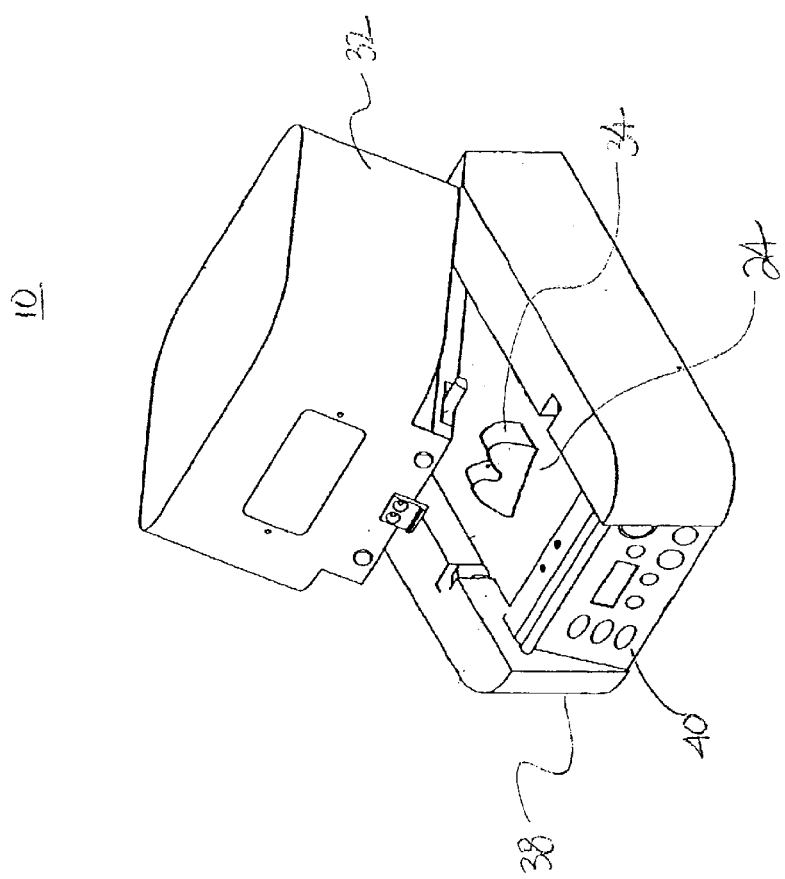
FIG. 1 is perspective view of a curing apparatus of the present invention.
Figure 3:
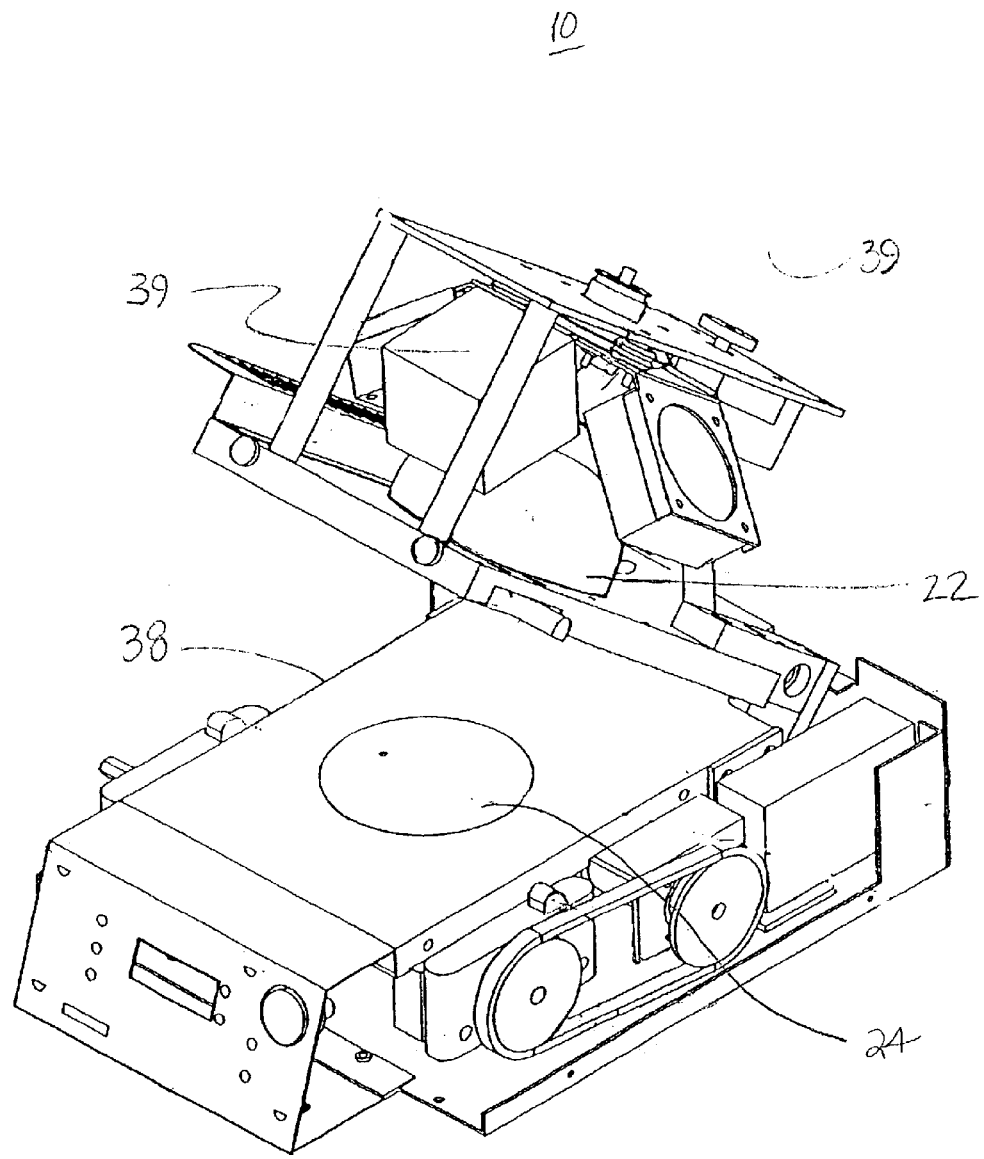
FIG. 3 a perspective view of the apparatus of FIG. 1 showing the internal components.

FIGS. 1 and 3 show a curing apparatus 10 for curing dental materials in a variety of modes including light alone, pressure alone (does not cure, but can be used to reduce porosity), light and pressure in combination, and a purge cycle to be used with light and pressure.

Figure 4:
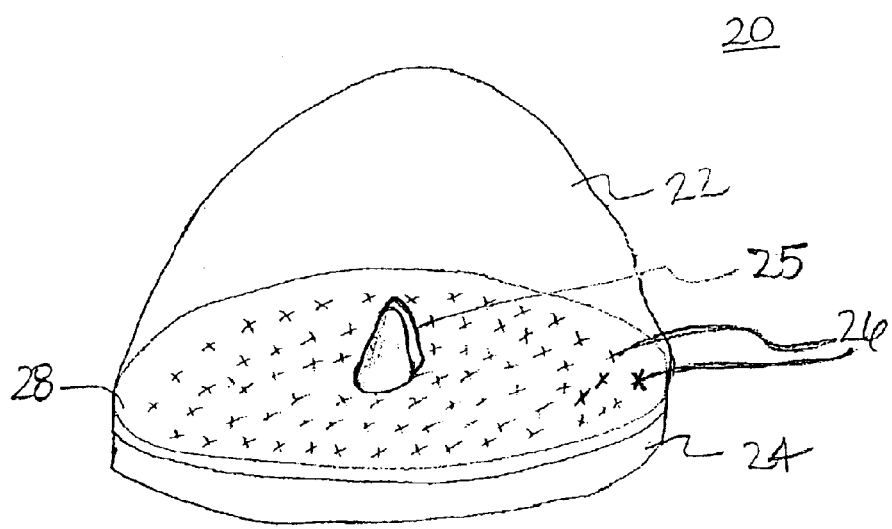
FIG. 4 is perspective view of a curing chamber having LEDs positioned in the floor of the chamber.

Curing apparatus 10 provides a facile method of curing by providing a curing chamber, which is preferably an air-tight chamber, 20, shown in FIG. 4. The curing chamber, includes a cover 22, which is preferably dome-shaped and is located in a cover or top section 32 of the curing apparatus, and a base 24 which is part of the base or bottom section 38 of the curing apparatus. A work piece 25 may be placed on base 24 of bottom section 38 when a curing operation is to be performed.

Figure 2:
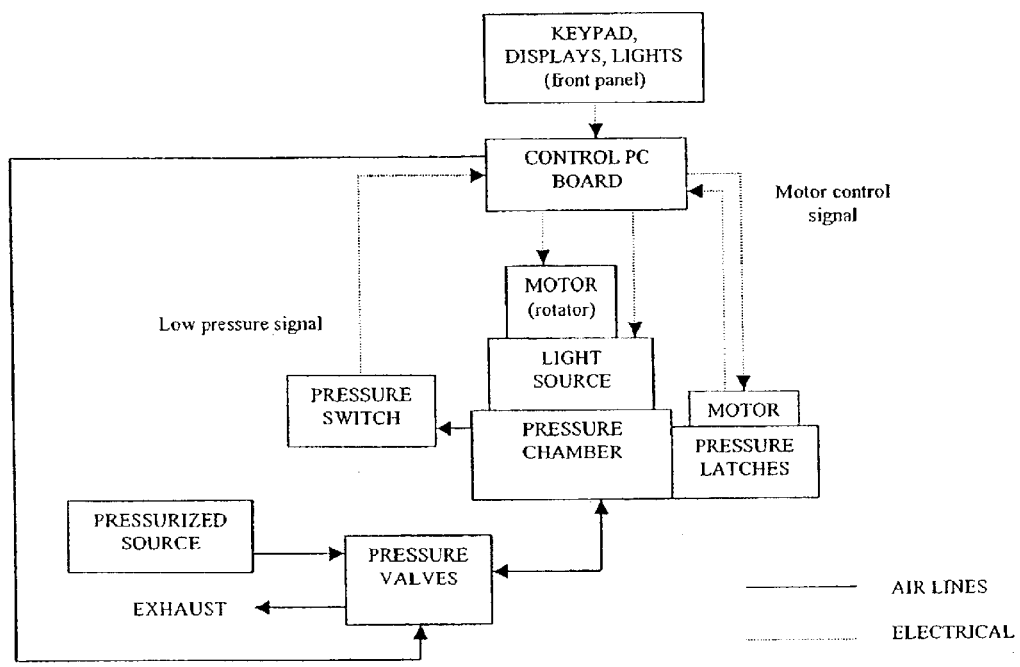
FIG. 2 is a block diagram showing the electrical connections and air line connections of the apparatus of FIG. 1.

FIG. 2 is provided to show the electrical connections and air or gas line layout. The front panel 40 is the control panel that is operatively associated with a processing device located internally. The control panel receives input from an operator relating to the light source and the gas source. The processing device is operatively associated with the light source and the gas source for controlling curing of the dental material by light and pressure within the air-tight chamber. The processing device may include, but is not limited to, a microprocessor, a microcontroller, a microcomputer, a controller, a digital signal processor, a central processing unit (CPU), or an application specific integrated circuit (ASIC). The processing device may be configured to cause gas to supply gas under pressure to the air-tight chamber prior to the time the light source supplies light to the chamber. It may be further configured to cause gas pressure to be maintained in the chamber at a constant level during the time the light source supplies light to the chamber. The processing device may be configured to cause the gas pressure to be initially supplied and subsequently released at least twice in succession, followed by application of pressure, whereby gas pressure is maintained at a constant level with in the chamber during the time the light source supplies light to the chamber.

FIG. 3 shows a light source comprising two lamps 39 arranged above cover 22, which cover may be transparent, positioned over base 24 of bottom section 38, which can create air-tight chamber 20 when in closed position. The lamps may comprise light emitting diodes, tungsten, halogen, mercury vapor, short arc xenon, or a metal halide source. The light source may comprise one or a plurality of lamps directed at base 24. Preferably, the spectral output of the lamp utilized herein is in the range of between about 380 nm to about 550 nm. Most preferably, the lamps comprise light emitting diodes. The LEDs may be positioned in a variety of ways to provide optimal curing of dental components The operation and the components of this curing apparatus are set forth in U.S. patent application Ser. No. 10/120, 934, filed Apr. 11, 2002, which is hereby incorporated by reference.

In accordance with one embodiment herein, FIG. 4 shows the LEDs 26 positioned on base 24. Polymerizable material 25 is placed on base 24 and dome cover 22 is positioned thereon. LEDs 26 located on base 24 may be covered by a protective transparent cover 28 to prevent any seepage of polymeric material onto the LEDs. LEDs 26 are optimally located on base 24 to provide direct application of light to the polymerizable material. Dome cover 22 may be transparent or opaque and may be covered with a reflective coating on the internal side to reflect any upwardly emitted light, down toward the polymerizable material. Base 24 acts as a heat sink for the power created by the LED semiconductor junction, reducing the need for cooling aids, such as fans.

Figure 5:
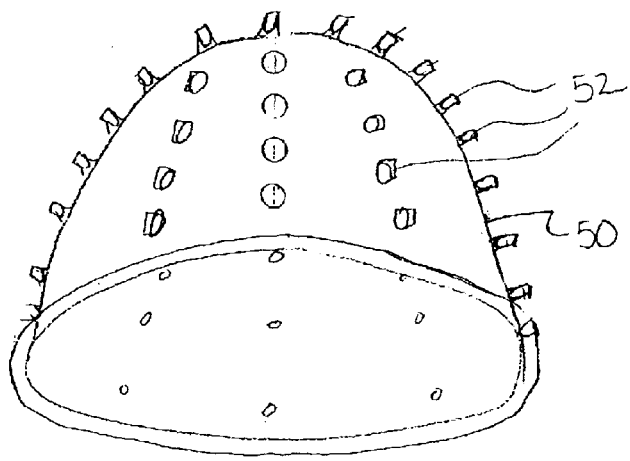
FIG. 5 is a perspective view of an alternate embodiment of a curing chamber having LEDs positioned on the dome cover.
Figure 6:
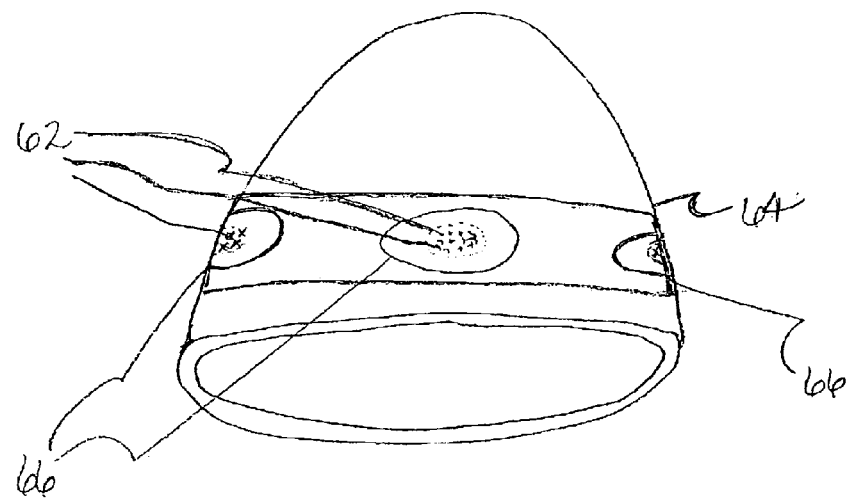
FIG. 6 is a perspective view of an alternate embodiment of a curing chamber having LEDs positioned on the dome cover.

In accordance with another embodiment, FIG. 5 shows a dome cover 50 with LEDs 52 mounted in cover 24 so that light is transmitted directly from the LEDs to the material being cured. LEDs may be mounted in a continuous pattern over the surface of cover 50. The LEDs may be mounted continuously as shown or in a variety of different patterns, as desired. FIG. 6 shows an alternate embodiment of a dome cover 50 having LEDS 62 mounted to cover 64 in a series of locations on the surface of cover 34. The LEDs 62 are shown mounted on a substrate 66 and substrates 66 may be mounted continuously along the lower surface as shown or in a variety of different patterns, as desired. In the embodiments shown in FIGS. 5 and 6, covers 50 and 64 may include a reflective internal surface on the areas where the LEDS are not located to provide reflectance of light to the material being cured.

Figure 7:
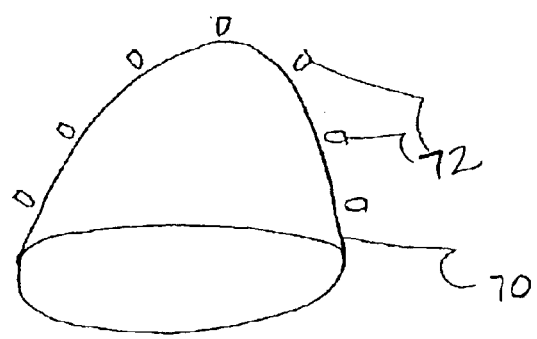
FIG. 7 is a perspective view of an alternate embodiment of a curing chamber having LEDs positioned along the perimeter of the dome cover.

In yet another embodiment herein, FIG. 7 shows dome cover 70 having LEDs 72 mounted along the perimeter of cover 70, so that light is transmitted through cover 70. LEDs 72 may be connected to cover 70 or may be independently located proximate cover 70. Cover 70 may be completely transparent or transparent only in those locations where the light is directed.

Figure 8:
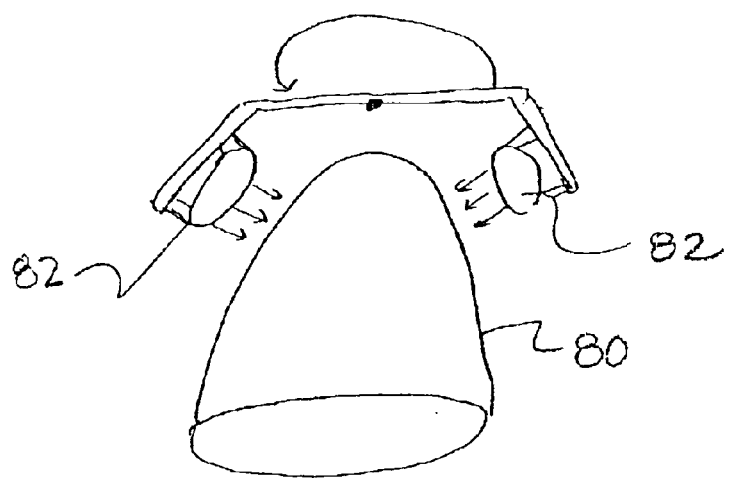
FIG. 8 is a perspective view of an alternate embodiment of a curing chamber having LEDs rotating about the curing dome.

FIG. 8 shows yet another embodiment of dome cover 80 having LEDs 82 located above cover 80 and rotatable around cover 80 to provide even and continuous light to the dental material being cured.

The wavelength of the LEDs used herein are in the wavelength range from about 380 to about 550 nanometers. Commercially available LEDs useful herein include Luxeon Star Power Light Source LEDs from Lumileds in San Jose, Calif. and Shark High Flux LED Illuminators from Opto Technology Inc. in Wheeling, Ill. The dome described herein in combination with the LEDs is used in a light curing apparatus or in a light and pressure curing apparatus. The dome is preferably used in a light curing apparatus or in a light and pressure curing apparatus such as that described in copending application Ser. No. 10/120,934, filed Apr. 11, 2002 entitled Curing Unit For Dental Materials, naming one common inventor, and is hereby incorporated by reference.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An apparatus for curing a polymerizable dental material comprising:

an air-tight chamber for receiving the dental material therein;

a light source for supplying light to an interior of the air-tight chamber;

a gas inlet for receiving pressurized gas into the interior of the air-tight chamber from an independent gas source;

a processing means operatively associated with the light source and the gas source for controlling curing of the dental material by light and pressure within the air-tight chamber; and a control means operatively associated with the processing means for receiving input from an operator relating to operation of the light source and the gas source;

wherein the light source comprises a plurality of LEDs positioned on the air-tight chamber.

2. The apparatus of claim 1 wherein the air-tight chamber comprises a base and a cover.

3. The apparatus of claim 2 wherein the plurality of LEDs are positioned on the base.

4. The apparatus of claim 2 wherein the plurality of LEDs are positioned on the cover.

5. The apparatus of claim 4 wherein the LEDs are mounted in the cover.

6. The apparatus of claim 4 wherein the LEDs are mounted uniformly on the cover.

7. The apparatus of claim 4 wherein the LEDs are mounted in selected areas on the cover.

8. The apparatus of claim 4 wherein the LEDs are mounted along a periphery of the cover.

9. The apparatus of claim 2 wherein the cover is transparent.

10. The apparatus of claim 2 wherein the cover comprises a reflective coating on an interior side.

11. The apparatus of claim 2 wherein the LEDs are positioned proximate the cover.

12. The apparatus of claim 11 wherein the LEDs rotate around a periphery of the cover.

13. An apparatus for curing a polymerizable dental material comprising:
  a curing chamber for receiving the dental material therein;
  a light source for supplying light to an interior of curing chamber;
  a processing means operatively associated with the light source for controlling curing of the dental material by light within the curing chamber; and
  a control means operatively associated with the processing means for receiving input from an operator relating to operation of the light source;
  wherein the light source comprises a plurality of LEDs positioned on the curing chamber.

14. The apparatus of claim 13 wherein the curing chamber comprises a base and a cover.

15. The apparatus of claim 14 wherein the plurality of LEDs are positioned on the base.

16. The apparatus of claim 14 wherein the plurality of LEDs are positioned on the cover.

17. The apparatus of claim 16 wherein the LEDs are mounted in the cover.

18. The apparatus of claim 16 wherein the LEDs are mounted uniformly on the cover.

19. The apparatus of claim 16 wherein the LEDs are mounted in selected areas on the cover.

20. The apparatus of claim 16 wherein the LEDs are mounted along a periphery of the cover.

21. The apparatus of claim 14 wherein the cover is transparent.

22. The apparatus of claim 14 wherein the cover comprises a reflective coating an interior side.

23. The apparatus of claim 14 wherein the LEDs are positioned proximate the cover.

24. The apparatus of claim 14 wherein the LEDs rotate around the periphery of the cover.

* * * * *